United States Patent
Li et al.

(10) Patent No.: US 10,130,516 B2
(45) Date of Patent: Nov. 20, 2018

(54) ELECTRONIC DEVICE FOR A DEAF PERSON (71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Mubing Li, Beijing (CN); Chungchun Chen, Beijing (CN); Xiaochuan Chen, Beijing (CN); Haisheng Wang, Beijing (CN); Jiantao Liu, Beijing (CN); Xue Dong, Beijing (CN); Jinghua Miao, Beijing (CN); Lin Lin, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 259 days.

(21) Appl. No.: 15/108,187

(22) PCT Filed: Oct. 27, 2015

(86) PCT No.: PCT/CN2015/092920
§ 371 (c)(1),
(2) Date: Jun. 24, 2016

(87) PCT Pub. No.: WO2016/192283
PCT Pub. Date: Dec. 8, 2016

(65) Prior Publication Data
US 2018/0193198 A1 Jul. 12, 2018

(30) Foreign Application Priority Data
Jun. 5, 2015 (CN) .......................... 2015 1 0305569

(51) Int. Cl.
*A61F 11/04* (2006.01)
*G01S 3/80* (2006.01)

(52) U.S. Cl.
CPC ............ *A61F 11/04* (2013.01); *A61F 11/045* (2013.01); *G01S 3/80* (2013.01)

(58) Field of Classification Search
CPC .......... A61F 11/00; A61F 11/04; A61F 11/08; A61F 11/045; H04R 25/00; H03G 3/20; H04L 27/06; G01S 3/80
(Continued)

(56) References Cited

U.S. PATENT DOCUMENTS

2002/0122560 A1   9/2002 An
2005/0157829 A1*  7/2005 Aoyama ................ G01R 29/26
                                                       375/376
(Continued)

FOREIGN PATENT DOCUMENTS

CN    1868428 A    11/2006
CN  101347368 A     1/2009
(Continued)

OTHER PUBLICATIONS

First Office Action regarding Chinese Application No. 201510305569. 3, dated Mar. 2, 2017. Translation provided by Dragon Intellectual Property Law Firm.
(Continued)

*Primary Examiner* — Hung T Nguyen
(74) *Attorney, Agent, or Firm* — Harness, Dickey & Pierce, P.L.C.

(57) ABSTRACT

An electronic device for a deaf person is provided. The device includes sound sensors arranged at different positions of the electronic device, and configured for sensing an external sound and converting the sensed external sound into sound signals; a processor connected to the sound sensors, and configured for generating a prompt signal when any sound parameters of the sound signals transmitted by the
(Continued)

sound sensors meets a prompt condition; a vibrator connected to the processor, and configured for vibrating upon receiving the prompt signals; a first comparator connected to the processor, and configured for, in response of receiving the prompt signal, determining a sound sensor corresponding to a sound signal with a highest intensity, and generating orientation information corresponding to the sound sensor that corresponds to the sound signal with the highest intensity; and an indicator connected to the first comparator, and configured for indicating the orientation information.

20 Claims, 8 Drawing Sheets (58) Field of Classification Search
USPC .............. 340/540, 539.11; 367/118; 375/376; 381/57
See application file for complete search history.

(56) References Cited

U.S. PATENT DOCUMENTS

2009/0323474 A1    12/2009   Lin

2014/0044269 A1    2/2014   Anderson
2014/0156032 A1*   6/2014   Jenkins ................... G05B 9/02
                                                                                             700/78

FOREIGN PATENT DOCUMENTS

| CN | 101401757 A | 4/2009 |
| --- | --- | --- |
| CN | 101614803 A | 12/2009 |
| CN | 202018703 U | 10/2011 |
| CN | 202871023 U | 4/2013 |
| CN | 103581803 A | 2/2014 |
| CN | 104865877 A | 8/2015 |
| CN | 204705850 U | 10/2015 |

OTHER PUBLICATIONS

Written Opinion of the International Searching Authority for International Application No. PCT/CN2015/092920 and International Search Report dated, Mar. 15, 2016. Translation provided by Dragon Intellectual Property Law Firm.

* cited by examiner

ELECTRONIC DEVICE FOR A DEAF PERSON

CROSS-REFERENCE TO RELATED APPLICATIONS

This application is the U.S. national phase of PCT Application No. PCT/CN2015/092920filed on Oct 27, 2015, which claims priority to Chinese Patent Application No. 201510305569.3filed in China on Jun 5, 2015, the disclosures of which are incorporated in their entirety by reference herein.

TECHNICAL FIELD

The present disclosure relates to the field of the electronic technique, in particular to an electronic device.

BACKGROUND

Due to loss of hearing, a deaf person cannot hear external sounds, which brings about much inconvenience for the deaf person. For example, in the presence of a whistle from a nearby motor vehicle on the road, a sound of a doorbell in a house or calling from someone, the deaf person cannot hear the sounds at all, let alone recognize from which direction the sounds come, and thus the deaf person cannot respond accordingly in time. Therefore, an insecurity factor is present.

SUMMARY

An object of the present disclosure is to provide an electronic device, so as to draw the deaf person's attention to a nearby sound and help him or her recognize from which direction the sounds come.

The present disclosure provides an electronic device, so as to prevent the deaf person from being in a parlous state due to the incapability of hearing a sound. The electronic device includes: a plurality of sound sensors arranged at different positions of the electronic device, and configured for sensing an external sound and converting the sensed external sound into sound signals; a processor connected to the sound sensors, and configured for generating a prompt signal in the case that any one of sound parameters of the sound signals transmitted by the sound sensors meets a prompt condition; a vibrator connected to the processor, and configured for vibrating upon receiving the prompt signals; a first comparator connected to the processor, and configured for, in response of receiving the prompt signal, determining a sound sensor that corresponds to a sound signal with a highest intensity by comparing intensities of the sound signals transmitted from the sound sensors, and generating orientation information corresponding to the sound sensor that corresponds to the sound signal with the highest intensity; and an indicator connected to the first comparator, and configured for indicating the orientation information.

Alternatively, the sound parameters are sound intensities, and the processor includes: a second comparator connected to the sound sensors, and configured for comparing each of the intensities of the sound signals transmitted by the sound sensors with a preset threshold value, and generating the prompt signal in the case that an intensity of any one of the sound signals is greater than or equal to the preset threshold value.

Alternatively, the sound parameters are sound frequencies, the electronic device further includes a first memory for storing the sound frequencies of preset sound sources, and the processor includes: a third comparator connected to the first memory, and configured for comparing frequencies of the sound signals transmitted by the sound sensors with the sound frequencies of the stored preset sources, and generating the prompt signal in the case that one of frequencies of the sound signals transmitted by the sound sensors is matched with one of the sound frequencies of the stored preset sound sources.

Alternatively, the indicator includes: indicator lights, each of which corresponds to a sound sensor, and is arranged at a position near the corresponding sound sensor; and a light driver connected to the first comparator, and configured for turning on an indicator light corresponding to the sound sensor that corresponds to the sound signal with the highest intensity according to the orientation information.

Alternatively, the indicator includes: a display screen; and a display driver connected to the first comparator, and configured for driving the display screen to display the orientation information.

Alternatively, the electronic device further includes: a first memory configured for storing sound frequencies of the preset sound sources, wherein the processor includes: a fourth comparator connected to the first memory, and configured for comparing the frequencies of the sound signals transmitted by the sound sensors with the sound frequencies of the stored preset sound sources, and generating a sound source prompt signal in the case that one of frequencies of the sound signals transmitted by the sound sensors is matched with one of the sound frequencies of the stored preset sound sources, wherein the sound source prompt signals includes information on the one of the preset sound sources; and the display driver is connected to the fourth comparator, and configured for driving the display screen to display the orientation information and the information on the one of the preset sound sources according to the orientation information and the sound source prompt signal.

Alternatively, the electronic device is a smart bracelet.

Alternatively, the plurality of sound sensors includes: four first sound sensors arranged on a strap of the smart bracelet symmetrically in pairs, and distributed evenly in a circumferential direction of the strap.

Alternatively, the plurality of sound sensors includes two second sound sensors arranged on the strap symmetrically in an axial direction of the bracelet.

Alternatively, the electronic device further includes: a mode setting module configured for setting the smart bracelet to be in a vertical arrangement mode or a horizontal arrangement mode; and a second memory configured for storing information on the sound sensors corresponding to the vertical arrangement mode and the horizontal arrangement mode, wherein the vertical arrangement mode corresponds to the four first sound sensors, and the horizontal arrangement mode corresponds to two first sound sensors that characterize front and rear positions and two second sound sensors that characterize left and right positions, wherein the first comparator is connected to the mode setting module and the second memory, and is further configured for: determining, in the case that the prompt signal is received and the smart bracelet is set to be in the vertical arrangement mode, the sound sensor corresponding to the sound signal with the highest intensity by comparing the intensities of the sound signals transmitted by the four first sound sensors, and generating the orientation information corresponding to the sound sensor that corresponds to the sound signal with the highest intensity, and determining, in the case that the prompt signal is received and the smart bracelet is set to be in the horizontal arrangement mode, the sound sensor corresponding to the sound signal with the highest intensity by comparing the intensities of the sound signals transmitted by the two first sound sensors that characterize the front and rear positions respectively and the two second sound sensors that characterize the left and right positions respectively, and generating the orientation information corresponding to the sound sensor that corresponds to the sound signal with the highest intensity.

Alternatively, the mode setting module includes a mode setting button or key arranged on the smart bracelet, and a user selects a current arrangement mode of the smart bracelet from the vertical arrangement mode and the horizontal arrangement mode by means of the mode setting button or key.

Alternatively, the mode setting module includes: a gyroscope configured for automatically detecting an arrangement mode of the smart bracelet, so as to determine whether the smart bracelet is in the vertical arrangement mode or the horizontal arrangement mode.

Alternatively, the electronic device is a handheld electronic device.

Alternatively, the electronic device is a wearable electronic device.

Alternatively, the display driver does not drive the display screen to function in the case that there is no preset sound source matched with any one of the frequencies of the sound signals transmitted by the sound sensors.

The above technical solution of the present disclosure has the following beneficial effects: when any one of the sound signals sensed by the sound sensors meets the condition, a vibrator vibrates to draw the deaf person's attention to nearby sounds. As a result, the deaf person can take actions in response to an accident in the ambience based on the vibration as well as the orientation indication indicating where the sounds come from provided by the indicator, so as to bring about great convenience for the deaf person.

BRIEF DESCRIPTION OF THE DRAWINGS

In order to illustrate the technical solutions of the present disclosure or the related art in a clearer manner, the drawings desired for the embodiments will be described briefly hereinafter. Obviously, the following drawings merely relate to some embodiments of the present disclosure, and based on these drawings, a person skilled in the art may obtain the other drawings without any creative effort.

DETAILED DESCRIPTION

The present disclosure will be described hereinafter in conjunction with the drawings and embodiments. The following embodiments are for illustrative purposes only, but shall not be used to limit the scope of the present disclosure.

In order to make the objects, the technical solutions and the advantages of the present disclosure more apparent, some technical solutions of the present disclosure will be described hereinafter in a clear and complete manner in conjunction with the drawings and embodiments. Obviously, the following embodiments are merely a part of, rather than all of, the embodiments of the present disclosure, and based on these embodiments, a person skilled in the art may obtain the other embodiments, which also fall within the scope of the present disclosure.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "a" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

In the following, it is clearly and completely described the technical solutions according to the embodiments of the present disclosure. It is obvious that the described embodiments are merely some of all the embodiment of the present disclosure instead of all the embodiment, and based on these embodiments, a person skilled in the art may obtain the other embodiments, which also fall within the scope of the present disclosure.

Figure 1:
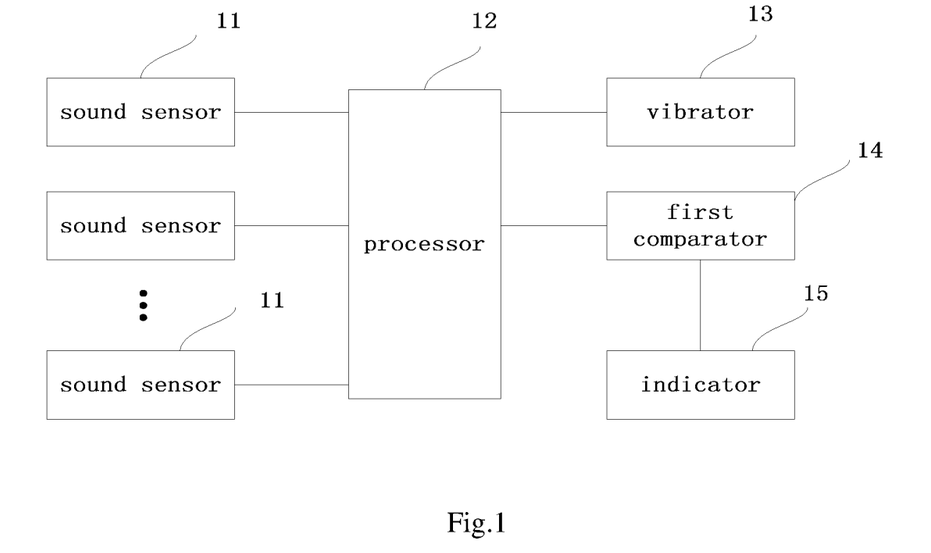
FIG. 1 is a schematic view showing an electronic device according to a first embodiment of the present disclosure.

Referring to FIG. 1, which is a schematic view showing an electronic device according to a first embodiment of the present disclosure. The electronic device includes:

a plurality of sound sensors 11 arranged at different positions of the electronic device, and configured for sensing an external sound and converting the sensed external sound into sound signals;

a processor 12 connected to the sound sensors 11, and configured for generating a prompt signal in the case that any one of the sound parameters of the sound signals transmitted by the sound sensors 11 meets a prompt condition;

a vibrator 13 connected to the processor 12, and configured for vibrating upon receiving the prompt signals;

a first comparator 14 connected to the processor 12, and configured for, in response of receiving the prompt signal, determining a sound sensor 11 that corresponds to a sound signal with a highest intensity by comparing intensities of the sound signals transmitted from the sound sensors 11, and generating orientation information corresponding to the sound sensor 11 that corresponds to the sound signal with the highest intensity; and an indicator 15 connected to the first comparator 14, and configured for indicating the orientation information.

By means of the electronic device provided in the above embodiment, when any one of the sound signals sensed by the sound sensors meets the condition, a vibrator vibrates to draw the deaf person's attention to nearby sounds. As a result, the deaf person can take appropriate measures in response to an accident in the ambience based on the vibration as well as the orientation indication indicating where the sounds come from provided by the indicator, so as to bring about great convenience for the deaf person.

Figure 2:
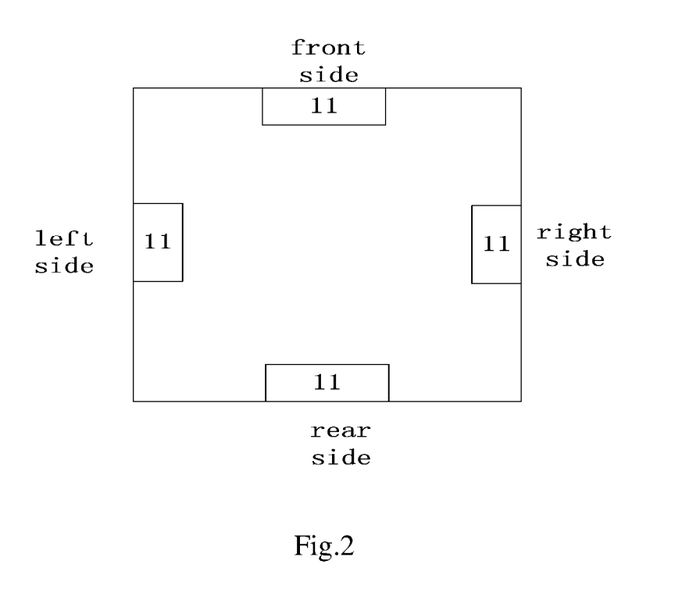
FIG. 2 is a schematic view showing an electronic device according to a second embodiment of the present disclosure.
Figure 3:
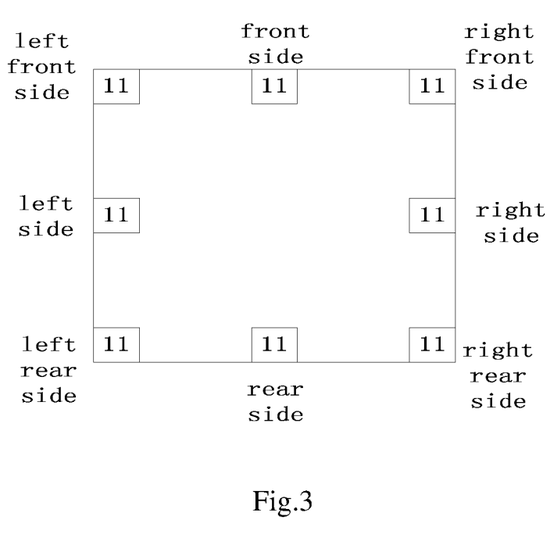
FIG. 3 is a schematic view showing an electronic device according to a third embodiment of the present disclosure.

Alternatively, the number of the sound sensors 11 is at least four. Referring to FIG. 2, in this embodiment, the electronic device includes four sound sensors 11, which respectively correspond to four orientations (the front, the rear, the left and the right sides). Surely, the number of the sound sensors 11 can be more than four. Referring to FIG. 3, in this embodiment, the electronic device includes eight sound sensors 11, which respectively correspond to eight orientations (the front, the rear, the left, the right, the left front, the left rear, the right front and the right rear sides).

In the embodiment of the present disclosure, the processor 12 generates the prompt signals when the sound parameters of the sound signals 11 transmitted by the sound sensors 11 meet the prompt condition.

In one embodiment, the sound parameters can be intensities of the sound signals, and the processor 12 may include:

a second comparator connected to the sound sensors 11, and configured for comparing each of the intensities of the sound signals transmitted by the sound sensors 11 with a preset threshold value, and generating the prompt signal in the case that an intensity of any one of the sound signals is greater than or equal to the preset threshold value.

That is, only when the intensity of any one of the sound signals sensed by the sound sensors 11 meets a certain intensity requirement, the processor 12 can determine that the sound signal is a useful, and then generate the prompt signal, and when each of the intensities of the sound signals sensed by the sound sensors 11 is relatively small, the processor 12 does not generate the prompt signal so as to avoid disturbance of the environmental noise.

In this embodiment, the processor 12 determines whether the intensities of the sound signals sensed by the sound sensors 11 meet the requirement. In other embodiments, the sound sensor 11 can determine the intensity of the sound signal sensed by itself. In other words, the sound sensor 11 compares the intensity of the sensed signal with the preset threshold value; when the intensity of the sensed signal is greater than or equal to the preset threshold value, it is converted into the sound signal and transmitted to the processor 12; and once the processor 12 receives the sound signal, it is determined that the sound parameter of the sound signal transmitted by the sound sensor 11 meets the prompt conditions, and then generates the prompt signals.

In another embodiment, the sound parameters are sound frequencies, the electronic device further includes a first memory for storing the sound frequencies of preset sound sources, and the processor 12 includes:

a third comparator connected to the first memory, and configured for comparing frequencies of the sound signals transmitted by the sound sensors 11 with the sound frequencies of the stored preset sources, and generating the prompt signal in the case that one of frequencies of the sound signals transmitted by the sound sensors 11 is matched with one of the sound frequencies of the stored preset sound sources.

For example, a whistle from a motor vehicle, a sound of a doorbell in the house, a calling from a family member and the like can be stored as the sound sources in advance, and then such sound sources are analyzed to obtain and store the sound frequencies of the sound sources. When it is determined that any one of the frequencies of the sound signals sensed by the sound sensors 11 is matched with any one of the frequencies of the stored sound sources by comparison, the prompt signal is generated, whereas no prompt is given for the other sound signal that are not matched with the stored sound sources, so as to filter out useless sounds.

It can be understood that the intensity of the electric sound signal sensed by the sound sensor closer to the sound source is greater. Therefore, in the embodiment of the present disclosure, the first comparator 14 determines the sound sensor 11 corresponding to the sound signal with the highest intensity by comparing the intensities of the sound signals transmitted by the plurality of sound sensors 11, and generates the orientation information corresponding to the sound sensor 11 that corresponds to the sound signal with the highest intensity, so as to indicate the orientation of the sound source.

Specifically, the first comparator 14 compares the intensities of the sound signals transmitted by the plurality of sound sensors 11 in pairs to determine the sound sensor 11 corresponding to the sound signal with the highest intensity.

Figure 4:
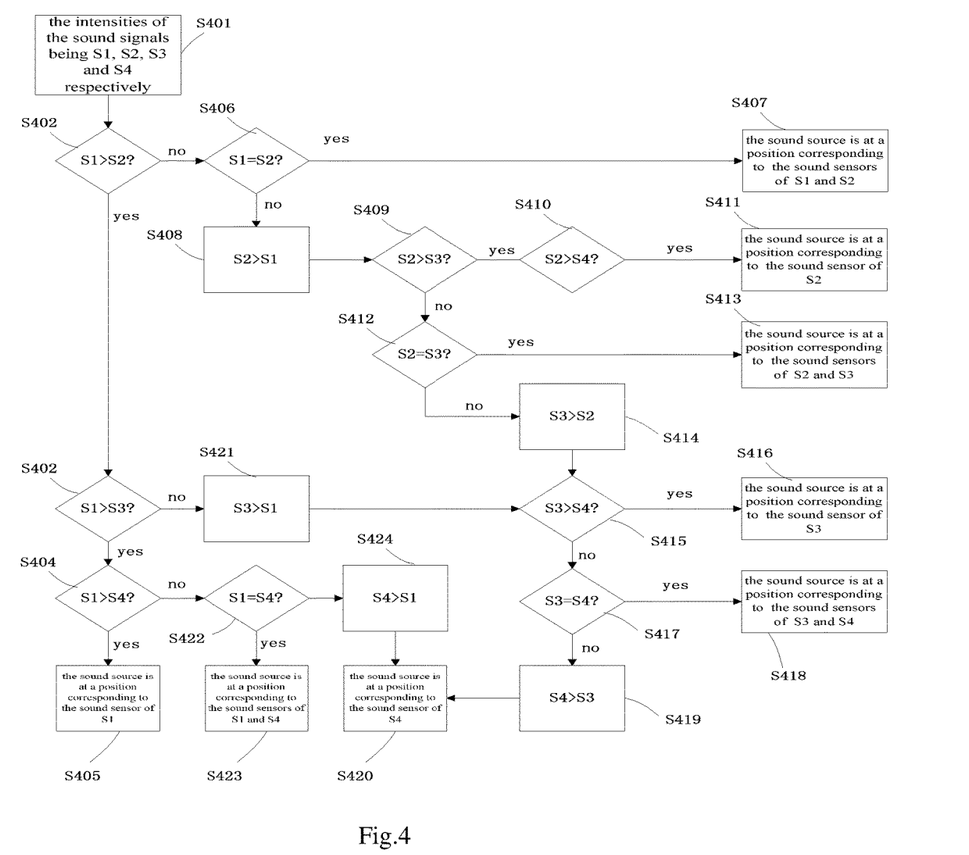
FIG. 4 is a flow chart about a method for determining an orientation of a sound source according to embodiments of the present disclosure.

For example, referring to FIG. 4, when the number of the sound sensors 11 is four, the first comparator 14 may determine the orientation of the sound source in a following procedure:

Step S401: setting the intensities of the sound signals corresponding to four sound sensors 11 to be S1, S2, S3 and S4 respectively;

Step S402: determining whether S1 is greater than S2; if it is, proceeding to Step S403; otherwise, proceeding to Step S406;

Step S403: determining whether S1 is greater than S3; if it is, proceeding to Step S404; otherwise, proceeding to Step S421;

Step S404: determining whether S1 is greater than S4; if it is, proceeding to Step S405; otherwise, proceeding to Step S422;

Step S405: determining that the orientation of the sound source is at a position corresponding to the sound sensor of the intensity S1;

Step S406: determining whether S1 is equal to S2; if it is, proceeding to Step S407; otherwise, proceeding to Step S408;

Step S408: determining S2 is greater than S1;

Step S409: determining whether S2 is greater than S3; if it is, proceeding to Step S410; otherwise, proceeding to Step S412;

Step S410: determining whether S2 is greater than S4; if it is, proceeding to Step S411; otherwise, proceeding to Step S4;

Step S411: determining that the orientation of the sound source is at a position corresponding to the sound sensor of the intensity S2;

Step S412: determining whether S2 is equal to S3; if it is, proceeding to Step S413; otherwise, proceeding to Step S414;

Step S413: determining that the orientation of the sound source is between positions corresponding to the sound sensors of the intensities S2 and S3;

Step S414: determining that S3 is greater than S2;

Step S415: determining whether S3 is greater than S4; if it is, proceeding to Step S416; otherwise, proceeding to Step S417;

Step S416: determining that the orientation of the sound source is at a position corresponding to the sound sensor of the intensity S3;

Step S417: determining whether S3 is equal to S4; if it is, proceeding to Step S418; otherwise, proceeding to Step S419;

Step S418: determining that the orientation of the sound source is between positions corresponding to the sound sensors of intensities S3 and S4;

Step S419: determining that S4 is greater than S3;

Step S420: determining that the orientation of the sound source is at a position corresponding to the sound sensor of the intensity S4;

Step S421: determining that S3 is greater than S1, and then proceeding to Step S415;

Step S422: determining whether S1 is equal to S4; if it is, proceeding to Step S423; otherwise, proceeding to Step S424;

Step S423: determining that the orientation of the sound source is between positions corresponding to the sound sensors of the intensities S1 and S4; and Step S424: determining that S4 is greater than S1, and then proceeding to Step S420.

In the embodiment of the present disclosure, the indicator 15 is configured for indicating the orientation of the sound source in one of a plurality of manner. An example is as follows.

Figure 5:
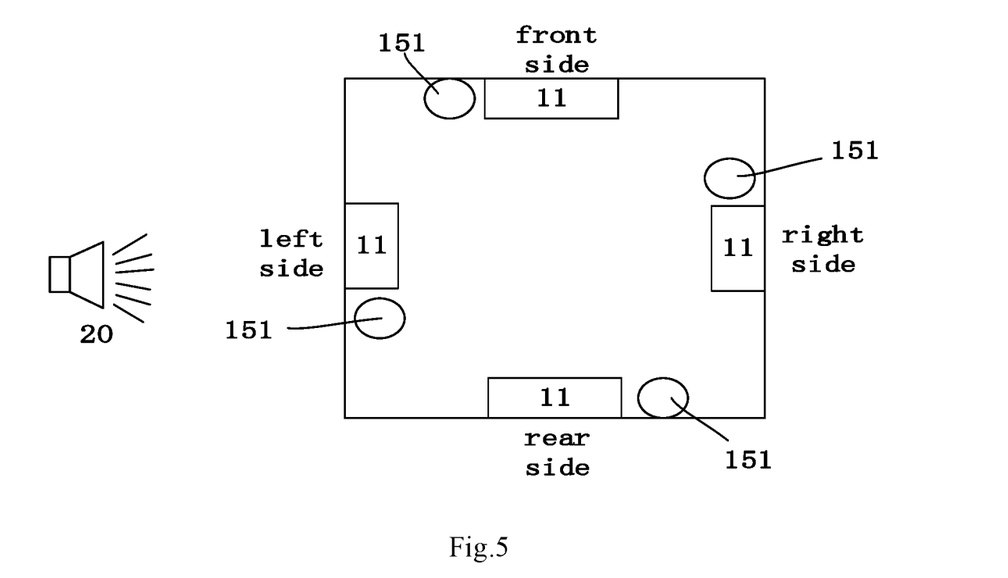
FIG. 5 is a schematic view showing an electronic device according to a fourth embodiment of the present disclosure.

In one embodiment, referring to FIG. 5, the indicator 15 may include:

indicator lights 151, each of which corresponds to a sound sensor 11, and is arranged at a position near the corresponding sound sensor 11; and a light driver (not shown) connected to the first comparator (not shown), and configured for turning on an indicator light 151 corresponding to the sound sensor 11 that corresponds to the sound signal with the highest intensity according to the orientation information.

In the embodiment shown in FIG. 5, four sound sensors 11 and four indicator lights 151 are included. The indicator light 151 correspond to the sound sensors 11 respectively, and each of the indicator light 151 is provided at a position near the corresponding sound sensor 11. The four sound sensors 11 represent four different directions respectively, wherein the sound sensor 11 at the upper side corresponds to the front side, the sound sensor 11 at the lower side corresponds to the rear side, the sound sensor 11 at the left side corresponds to the left side, and the sound sensor 11 at the right side corresponds to the right side.

When there is a sound source 20 nearby and any one of the sound signals sensed by the sound sensors 11 meets the prompt conditions, the vibrator (not shown) vibrates, and the first comparator compares the intensities of the sound signals transmitted by the four sound sensors 11 to determine the sound sensor 11 that corresponds to the sound signal with the highest intensity. In this figure, the sound source 20 is provided at the left side, and thus the sound signal sensed by the sound sensor 11 provided at the left side is of the highest intensity. At this time, the indicator light driver can turn the indicator light corresponding to the sound sensor 11 at the left side to draw the deaf person's attention to the orientation of the sound source.

Figure 6:
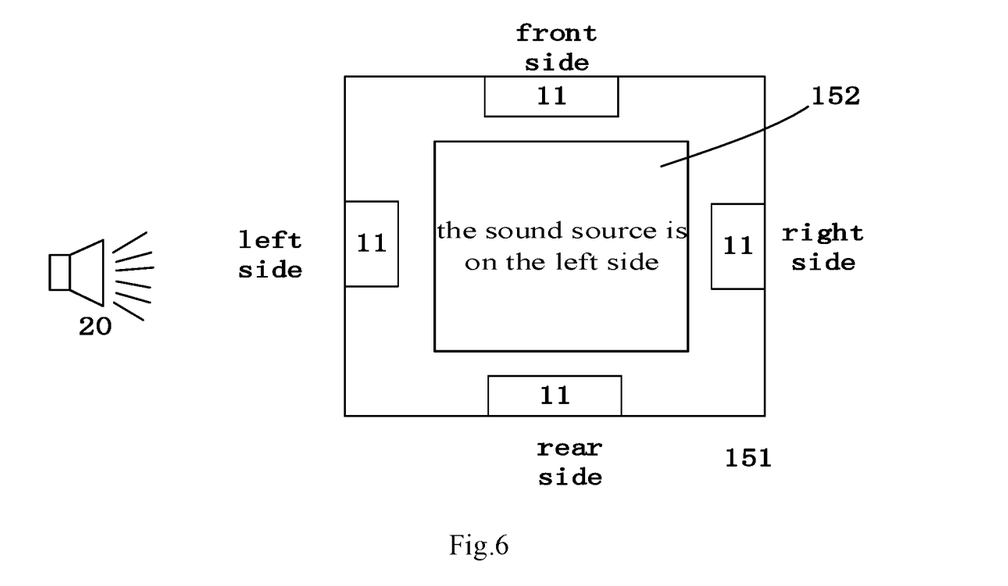
FIG. 6 is a schematic view showing an electronic device according to a fifth embodiment of the present disclosure.

In another embodiment, referring to FIG. 6, the indicator 15 may include:

a display screen 152; and a display driver (not shown) connected to the first comparator (not shown), and configured for driving the display screen 152 to display the orientation information.

In the embodiment shown in FIG. 6, four sound sensors 11 are included. The four sound sensors 11 correspond to different directions respectively, wherein the sound sensor 11 at the upper side corresponds to the front side, the sound sensor 11 at the lower side corresponds to the rear side, the sound sensor 11 at the left side corresponds to the left side, and the sound sensor 11 at the right side corresponds to the right side.

When there is the sound source 20 nearby and the sound signal sensed by the sound sensor 11 meets the prompt condition, the vibrator (not shown) vibrates, and the first comparator compares the intensities of the sound signals transmitted by the four sound sensors 11 to determine the sound sensor 11 that corresponds to the sound signal with the highest intensity. In the figure, the sound source 20 is provided at the left, and thus the sound signals sensed by the sound sensor 11 provided at the left side is of the highest intensity. At this time, the display driver drives the display screen 152 to display a content such as "the sound source is on the left side".

Alternatively, when the display screen 152, as the indicator, indicates the orientation information of the sound source, the electronic device further includes:

a first memory configured for storing the sound frequencies of the preset sound sources, wherein the preset sound source, for example, can be a whistle from a motor vehicle, a sound of a doorbell in the house, a calling from a family member and the like.

The processor includes: a fourth comparator connected to the first memory, and configured for comparing the frequencies of the sound signals transmitted by the sound sensors 11 with the sound frequencies of the stored preset sound sources, and generating a sound source prompt signal in the case that one of frequencies of the sound signals transmitted by the sound sensors is matched with one of the sound frequencies of the stored preset sound sources, wherein the sound source prompt signals includes information on the one of the preset sound sources.

The display driver is connected to the fourth comparator, and configured for driving the display screen to display the orientation information and the information on the one of the preset sound sources according to the orientation information and the sound source prompt signal.

For example, the display driver drives the display screen 152 to display a content such as "a whistle from a motor vehicle is on the left side", wherein "the whistle from the motor vehicle" is the information on the one of the preset sound sources matched with the one of the frequencies of the sound signals transmitted by the sound sensors, and "on the left side" indicates the orientation information corresponding to the sound sensor that corresponds to the sound signal with the highest intensity.

Figure 7:
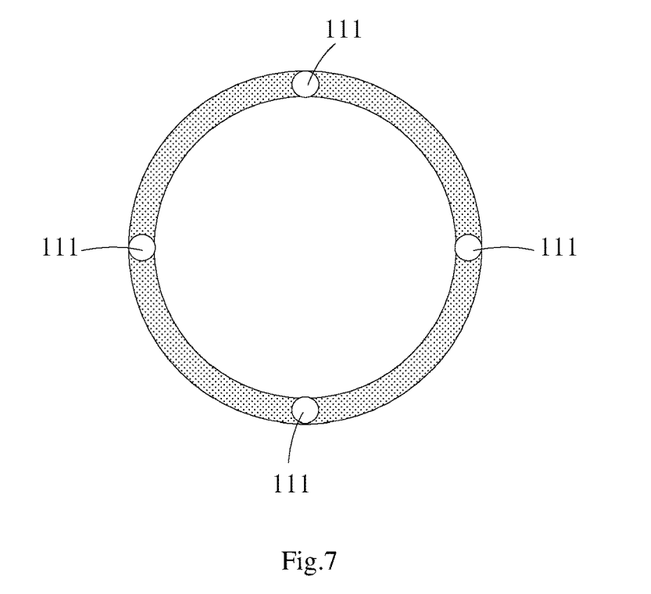
FIG. 7 is a schematic view showing a smart bracelet according to a sixth embodiment of the present disclosure.
Figure 8:
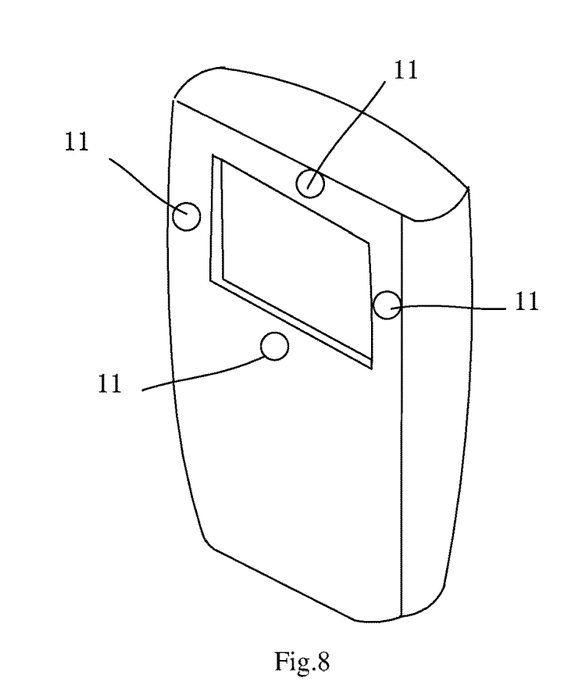
FIG. 8 is a schematic view showing a handheld electronic device according to a seventh embodiment of the present disclosure.

Referring to FIG. 7, the electronic device in the above embodiment can be a smart bracelet, which is worn around the wrist of the deaf person. Alternatively, referring to FIG. 8, the electronic device can be a handheld electronic device, which is handheld by the deaf person. Alternatively, the electronic device can be a smart ring worn around the finger or another wearable device such as a smart accessory worn in front of the chest of the deaf person.

FIG. 7 shows an embodiment in which the electronic device is the smart bracelet. The bracelet includes a plurality of sound sensors, which include four first sound sensors 111. The four first sound sensors 111 are arranged on a strap of the smart bracelet symmetrically in pairs, and distributed evenly in a circumferential direction of the strap.

Figure 9:
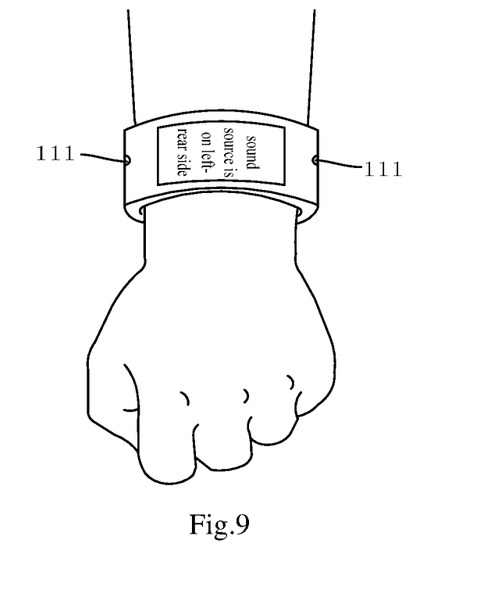
FIG. 9 is a schematic view showing a vertical arrangement mode of a smart bracelet according to the seventh embodiment of the present disclosure.

Referring to FIG. 9, when a user walks or stands still, his or her arm is generally in a state of vertical placement. When the user wears the smart bracelet, one of the four first sound sensors 111 can be used to correspond to the front side, and another one symmetrically provided with it can be used to correspond to the rear side. In addition, the rest two sensors that are symmetrically provided may correspond to the left and the right sides respectively. The orientation information corresponding to the first sound sensor 111 needs to be stored in the smart bracelet. FIG. 9 only shows two first sound sensors 111 that correspond to the left and the right sides respectively, and the two first sound sensors 111 corresponding to the front and the rear sides are not shown due to the fact that one of which is shaded by the display screen and the other one is shaded by the arm.

By means of the four first sound sensors 111 and the above functional modules described in the above embodiment, when any one of the sound signals sensed by the first sound sensors meets the condition, the vibrator vibrates to give a reminder so as to draw the deaf person's attention to the nearby sound, and the indicator is used to indicate the orientation where the sounds come from.

Figure 10:
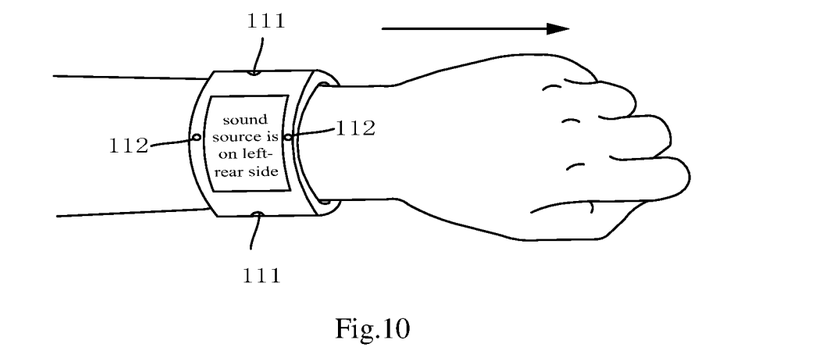
FIG. 10 is a schematic view showing the smart bracelet according to an eighth embodiment of the present disclosure.

Surely, in some situations, as shown in FIG. 10, the arm of the user may be in a state of horizontal placement. When the arm of the user is in a state of horizontal placement, the orientation corresponding to the first sound sensor is changed accordingly. As a result, if a prompt is given according to the orientation information corresponding to the stored first sound sensor 111, an error occurs.

Therefore, alternatively, referring to FIG. 10, the plurality of sound sensors further include two second sound sensors 112 arranged on the strap symmetrically in an axial direction of the bracelet (i.e. the direction indicated by the arrow in FIG. 10), wherein the two first sound sensors 111 previously corresponding to the left and the right sides now may correspond to the front and the rear sides respectively, while the two second sound sensors 112 correspond to the left and the right sides respectively.

At this time, the electronic device may further include:

a mode setting module configured for setting the smart bracelet to be in a vertical arrangement mode corresponding to a vertical placement of the user's arm or a horizontal arrangement mode corresponding to a horizontal placement of the user's arm; and a second memory configured for storing information on the sound sensors corresponding to the vertical arrangement mode and the horizontal arrangement mode, wherein the vertical arrangement mode corresponds to the four first sound sensors, and the horizontal arrangement mode corresponds to two first sound sensors that characterize front and rear positions respectively and two second sound sensors that characterize left and right positions respectively, wherein the first comparator is connected to the mode setting module and the second memory, and is further configured for: determining, in the case that the prompt signal is received and the smart bracelet is set to be in the vertical arrangement mode, the sound sensor corresponding to the sound signal with the highest intensity by comparing the intensities of the sound signals transmitted by the four first sound sensors, and generating the orientation information corresponding to the sound sensor that corresponds to the sound signal with the highest intensity, and determining, in the case that the prompt signal is received and the smart bracelet is set to be in the horizontal arrangement mode, the sound sensor corresponding to the sound signal with the highest intensity by comparing the intensities of the sound signals transmitted by the two first sound sensors that characterize the front and rear positions respectively and the two second sound sensors that characterize the left and right positions respectively, and generating the orientation information corresponding to the sound sensor that corresponds to the sound signal with the highest intensity.

In the above embodiment, the mode setting module includes a mode setting button or key arranged on the smart bracelet, and a user selects a current arrangement mode of the smart bracelet from the vertical arrangement mode and the horizontal arrangement mode by means of the mode setting button or key. In addition, the mode setting module includes: a gyroscope configured for automatically detecting an arrangement mode of the smart bracelet, so as to determine whether the smart bracelet is in the vertical arrangement mode or the horizontal arrangement mode.

Figure 11:
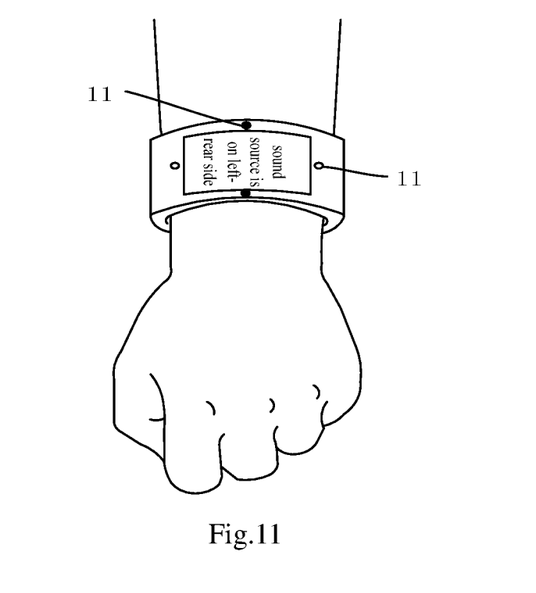
FIGS. 11 and 12 are schematic views showing the smart bracelet according to a ninth embodiment of the present disclosure.
Figure 12:
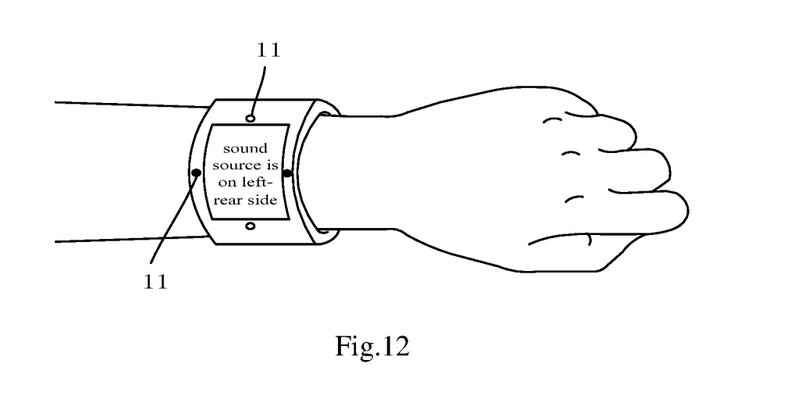

In the above embodiment, different sound sensors are used to sense the sounds in the vertical arrangement mode or in the horizontal arrangement mode. In some other embodiments of the present disclosure, the same sound sensors may be used to sense the sounds in the vertical arrangement mode and in the horizontal arrangement mode. For example, referring to FIGS. 11 and 12, the smart bracelet includes four sound sensors 11. When the bracelet is in the vertical arrangement mode, two sound sensors 11 indicated by the black solid circles may characterize the front and rear positions respectively, and two sound sensors 11 indicated by the empty circles characterize the left and right positions respectively. When the bracelet is in the horizontal arrangement mode, the two sound sensors 11 indicated by the black solid circles may characterize the left and right positions respectively, and the two sound sensors 11 indicated by the empty circles may characterize the front and rear positions respectively.

Figure 13:
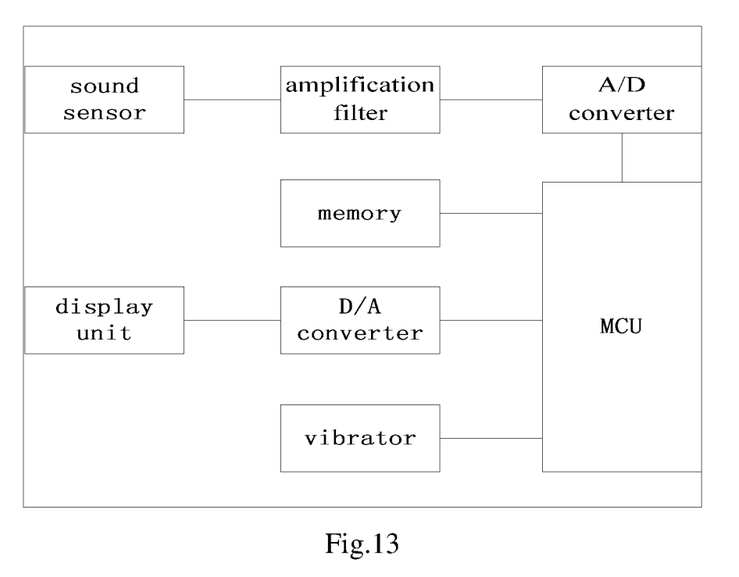
FIG. 13 is a schematic view showing an electronic device according to a tenth embodiment of the present disclosure.

FIG. 13 is a schematic view showing an electronic device according to an embodiment of the present disclosure. As shown in FIG. 13, the electronic device includes four sound sensors, an amplification filter, an analog-to-digital (A/D) converter, a micro processor unit (MCU), a random access memory (RAM), a digital-to-analog (D/A) converter, a display unit and a vibrator.

The four sound sensors are arranged at different positions of the electronic device, and configured for sensing an external sound and converting the sensed external sound into sound signals, which are electric signals.

The amplification filter is connected to the sound sensor and configured for amplifying and filtering the sound signals transmitted by the sound sensors.

The A/D converter is connected to the amplification filter and configured for converting the sound signals being the analog signal processed by the amplification sensor into the digital signals.

The MCU is connected to the A/D converter, and is configured for generating the prompt signals when any one of the sound parameters of the sound signal sensed by the sound sensor meets the prompt condition, and determining the sound sensor corresponding to the sound signal with the highest intensity by comparing the intensities of the sound signals transmitted by the four sound sensors, and generating the orientation information corresponding to the sound sensor that corresponds to the sound signal with the highest intensity. The functions of the MCU are similar to the functions of the processor and the first comparator in the previous embodiments.

The vibrator is connected to the micro processor unit, and vibrates after receiving the prompt signal.

The D/A converter is connected to the MCU, and configured for converting the orientation information into the analog display signal.

The display unit is connected to the D/A converter, and configured for displaying the mode display signal. The display unit includes the display screen and the display driver for driving the display screen.

The memory is connected to the MCU, and may store the orientation information corresponding to each sound sensor as well as the information such as the frequencies of the preset sound sources.

The above are merely the preferred embodiments of the present disclosure. It should be appreciated that, a person skilled in the art may make further modifications and improvements without departing from the principle of the present disclosure, and these modifications and improvements shall also fall within the scope of the present disclosure.

What is claimed is:

1. An electronic device for a deaf person, comprising:
   a plurality of sound sensors arranged at different positions of the electronic device, and configured for sensing an external sound and converting the sensed external sound into sound signals;
   a processor connected to the sound sensors, and configured for generating a prompt signal in a case that any one of sound parameters of the sound signals transmitted by the sound sensors meets a prompt condition;
   a vibrator connected to the processor, and configured for vibrating upon receiving the prompt signal;
   a first comparator connected to the processor, and configured for, in response of receiving the prompt signal, determining a sound sensor that corresponds to a sound signal with a highest intensity by comparing intensities of the sound signals transmitted from the sound sensors, and generating orientation information corresponding to the sound sensor that corresponds to the sound signal with the highest intensity; and
   an indicator connected to the first comparator, and configured for indicating the orientation information as where the sound signal comes from is provided to the deaf person.

2. The electronic device according to claim 1, wherein the sound parameters are sound intensities, and the processor comprises:
   a second comparator connected to the sound sensors, and configured for comparing each of the intensities of the sound signals transmitted by the sound sensors with a preset threshold value, and generating the prompt signal in the case that an intensity of any one of the sound signals is greater than or equal to the preset threshold value.

3. The electronic device according to claim 1, wherein the sound parameters are sound frequencies, the electronic device further comprises a first memory configured for storing the sound frequencies of preset sound sources, and the processor comprises:
   a third comparator connected to the first memory, and configured for comparing frequencies of the sound signals transmitted by the sound sensors with the sound frequencies of the stored preset sources, and generating the prompt signal in the case that one of frequencies of the sound signals transmitted by the sound sensors is matched with one of the sound frequencies of the stored preset sound sources.

4. The electronic device according to claim 2, wherein the indicator comprises:
   indicator lights, each of which corresponds to a sound sensor, and is arranged at a position near the corresponding sound sensor; and
   a light driver connected to the first comparator, and configured for turning on an indicator light corresponding to the sound sensor that corresponds to the sound signal with the highest intensity according to the orientation information.

5. The electronic device according to claim 2, wherein the indicator comprises:
   a display screen; and
   a display driver connected to the first comparator, and configured for driving the display screen to display the orientation information.

6. The electronic device according to claim 5, further comprising a first memory configured for storing sound frequencies of the preset sound sources, wherein
   the processor comprises: a fourth comparator connected to the first memory, and configured for comparing the frequencies of the sound signals transmitted by the sound sensors with the sound frequencies of the stored preset sound sources, and generating a sound source prompt signal in the case that one of frequencies of the sound signals transmitted by the sound sensors is matched with one of the sound frequencies of the stored preset sound sources, wherein the sound source prompt signal includes information on the one of the preset sound sources; and
   the display driver is connected to the fourth comparator, and configured for driving the display screen to display the orientation information and the information on the one of the preset sound sources according to the orientation information and the sound source prompt signal.

7. The electronic device according to claim 5, wherein the electronic device is a smart bracelet.

8. The electronic device according to claim 7, wherein the plurality of sound sensors comprises:
   four first sound sensors arranged on a strap of the smart bracelet symmetrically in pairs, and distributed evenly in a circumferential direction of the strap.

9. The electronic device according to claim 8, wherein the plurality of sound sensors further comprises:
   two second sound sensors arranged on the strap symmetrically in an axial direction of the smart bracelet.

10. The electronic device according to claim 9, further comprising
    a mode setting module configured for setting the smart bracelet to be in a vertical arrangement mode or a horizontal arrangement mode; and
    a second memory configured for storing information on the sound sensors corresponding to the vertical arrangement mode and the horizontal arrangement mode, wherein the vertical arrangement mode corresponds to the four first sound sensors, and the horizontal arrangement mode corresponds to two first sound sensors that characterize front and rear positions respectively and two second sound sensors that characterize left and right positions respectively, wherein the first comparator is connected to the mode setting module and the second memory, and is further configured for:
  determining, in the case that the prompt signal is received and the smart bracelet is set to be in the vertical arrangement mode, the sound sensor corresponding to the sound signal with the highest intensity by comparing the intensities of the sound signals transmitted by the four first sound sensors, and generating the orientation information corresponding to the sound sensor that corresponds to the sound signal with the highest intensity, and
  determining, in the case that the prompt signal is received and the smart bracelet is set to be in the horizontal arrangement mode, the sound sensor corresponding to the sound signal with the highest intensity by comparing the intensities of the sound signals transmitted by the two first sound sensors that characterize the front and rear positions respectively and the two second sound sensors that characterize the left and right positions respectively, and generating the orientation information corresponding to the sound sensor that corresponds to the sound signal with the highest intensity.

11. The electronic device according to claim 10, wherein the mode setting module comprises a mode setting button or key arranged on the smart bracelet, and a user selects a current arrangement mode of the smart bracelet from the vertical arrangement mode and the horizontal arrangement mode by means of the mode setting button or key.

12. The electronic device according to claim 10, wherein the mode setting module comprises: a gyroscope configured for automatically detecting an arrangement mode of the smart bracelet, so as to determine whether the smart bracelet is in the vertical arrangement mode or the horizontal arrangement mode.

13. The electronic device according to claim 4, wherein the electronic device is a handheld electronic device.

14. The electronic device according to claim 4, wherein the electronic device is a wearable electronic device.

15. The electronic device according to claim 6, wherein the display driver does not drive the display screen to function in the case that there is no preset sound source matched with any one of the frequencies of the sound signals transmitted by the sound sensors.

16. The electronic device according to claim 3, wherein the indicator comprises:
  indicator lights, each of which corresponds to a sound sensor, and is arranged at a position near the corresponding sound sensor; and
  a light driver connected to the first comparator, and configured for turning on an indicator light corresponding to the sound sensor that corresponds to the sound signal with the highest intensity according to the orientation information.

17. The electronic device according to claim 3, wherein the indicator comprises:
  a display screen; and
  a display driver connected to the first comparator, and configured for driving the display screen to display the orientation information.

18. The electronic device according to claim 16, wherein the electronic device is a handheld electronic device.

19. The electronic device according to claim 5, wherein the electronic device is a handheld electronic device.

20. The electronic device according to claim 5, wherein the electronic device is a wearable electronic device.

* * * * *